(12) United States Patent
Hittin

(10) Patent No.: US 6,615,538 B2
(45) Date of Patent: Sep. 9, 2003

(54) PROCESS AND APPARATUS FOR PROMOTING THE GERMINATION OF PLANT SEEDS AND THE PRODUCTION OF AGRICULTURAL CROPS

(75) Inventor: Zeev H. Hittin, Beer-Sehva (IL)

(73) Assignee: Seed-Tech Temed Ltd, Arava (IL)

(*) Notice: Subject to any disclaimer, the term of this patent is extended or adjusted under 35 U.S.C. 154(b) by 0 days.

(21) Appl. No.: 09/911,669

(22) Filed: Jul. 24, 2001

(65) Prior Publication Data

US 2002/0046488 A1 Apr. 25, 2002

Related U.S. Application Data (63) Continuation-in-part of application No. PCT/IL00/00146, filed on Mar. 9, 2000.

(30) Foreign Application Priority Data

Mar. 15, 1999 (IL) .................................................. 129004

(51) Int. Cl.[7] .............................................................. A01C 1/02
(52) U.S. Cl. ................................................................. 47/61
(58) Field of Search ....................................... 47/61, 60

(56) References Cited

U.S. PATENT DOCUMENTS

| | | | | |
|---|---|---|---|---|
| 3,327,425 A | * | 6/1967 | Dosedla et al. ............... | 47/60 |
| 3,670,193 A | * | 6/1972 | Thorington et al. ......... | 313/112 |
| 3,824,736 A | * | 7/1974 | Davis .......................... | 47/17 |
| 3,876,907 A | * | 4/1975 | Widmayer .................. | 315/208 |
| 3,940,885 A | | 3/1976 | Gray ............................ | 47/58 |
| 4,396,872 A | * | 8/1983 | Nutter ........................ | 315/308 |
| 4,642,939 A | | 2/1987 | Suzuki ......................... | 47/14 |
| 4,821,455 A | * | 4/1989 | Omente ....................... | 47/14 |
| 4,914,858 A | | 4/1990 | Nijssen et al. ............... | 47/58 |
| 5,012,609 A | | 5/1991 | Ignatius et al. ............... | 47/58 |
| 5,321,907 A | * | 6/1994 | Ueno et al. .................. | 206/423 |
| 5,722,118 A | | 3/1998 | Hansen et al. ............ | 16/114 R |
| 5,835,206 A | * | 11/1998 | Tragesser ................... | 356/406 |
| 2002/0046488 A1 | * | 4/2002 | Hittin ........................... | 47/61 |

FOREIGN PATENT DOCUMENTS

| | | | | |
|---|---|---|---|---|
| DE | 19928768 C1 | * | 7/2000 | |
| EP | 0 307 991 A1 | | 3/1989 | ............ A01G/7/04 |
| FR | 2490063 | | 3/1982 | ............ A01C/1/00 |
| GB | 1302613 | | 1/1973 | ............ A01G/9/00 |
| GB | 1379116 | | 1/1975 | ............ B02B/5/00 |
| GB | 2140262 A | | 11/1984 | ............ A01G/9/00 |
| GB | 2163634 A | * | 3/1986 | |
| GB | 2220551 A | | 1/1990 | ............ A01G/7/00 |
| GB | 2276525 A | | 10/1994 | ............ A01C/1/00 |
| JP | 2000050706 A | * | 2/2000 | ............ A01C/1/08 |
| RU | 2109429 C1 | * | 4/1998 | |
| SU | 1814494 A3 | * | 5/1993 | |
| WO | WO 84/00693 | | 3/1984 | ............ A61N/5/06 |
| WO | WO 98/14046 | * | 4/1998 | |

\* cited by examiner

*Primary Examiner*—Charles T. Jordan
*Assistant Examiner*—Jeffrey L. Gellner
(74) *Attorney, Agent, or Firm*—Baker Botts LLP (57) ABSTRACT

Method and apparatus for promoting by light irradiation the germination of seeds and the growth of plants generated by the seeds. The seeds to be treated are irradiated with radiation that is a simulation of the solar visible spectrum. The radiation may have a wavelength range from about 400 to about 700 nm. The irradiating light may be pulsed, for example at a frequency from about 10 to 150 pulses per minute, each pulses having a duration from 0.1 to 0.9 seconds and the intervals between pulses having a duration about from 0.1 to 6.0 seconds. The seeds may be cooled while irradiating them, such as to maintain the seeds at temperatures not exceeding 35° C. Cooling the seeds may be carried out by means of a stream of gas.

18 Claims, 12 Drawing Sheets

PROCESS AND APPARATUS FOR PROMOTING THE GERMINATION OF PLANT SEEDS AND THE PRODUCTION OF AGRICULTURAL CROPS

CROSS-REFERENCE TO RELATED APPLICATION

This application is a continuation-in-part of International Application PCT/IL00/00146 filed Mar. 9, 2000, which International Application was published in English by the International Bureau on Sep. 21, 2000, which claims the priority of Israel Patent Application No. 129004, filed Mar. 15, 1999.

FIELD OF THE INVENTION

This invention relates to a method and apparatus for promoting the germination of plant seeds and improving the production of agricultural crops, particularly for accelerating the germination of the seeds, accelerating the growth of the crops and improving their quantity and quality.

It is known that irradiation of seeds and plants may have an effect on plant growth and development. This effect is not univocal: e.g., irradiation of plant seeds may accelerate or retard their growth.

WO 84/00693, generally directed to improving the growth rate and production of animals by irradiation, also mentions a method whereby lamps producing infrared light having wavelengths falling between 600–670 nm are used as a source of illumination for horticulture and plant production. What results are obtained by said method, is not stated. Further, no information is given relative to its parameters, except for the wavelengths, nor is any example described.

U.S. Pat. No. 4,914,858 proposes a method for fostering growth of plant-propagating material by irradiation by means of light-emitting diodes (LEDs) and states that by a correctly chosen wavelength, energy consumption can be reduced and plant growth can be furthered in entirely darkened, closed accommodations. While it is generally stated that the light spectrum of the light sources used may lie between 400 and 800 nm, viz., in the visible spectrum slightly and in part in the infrared, it is said that the spectrum of approximately 660 nm, viz., infrared light, is optimal for rapid germination of seeds. It is further stated that it is possible to use an intermittent light source at high frequency, because plants have a certain slowness in reacting to light and therefore the intermittent lighting is sensed as more or less continuous and the speed of germination is not adversely affected thereby. No other details as to the method and its results are given. An apparatus is shown in which seeds are accommodated in various trays and a group of lights is situated above each tray.

The aforesaid prior publications, and the art in general, do not provide sufficient data and parameters for obtaining an efficient promotion of germination of seeds and growth crops by means of lighting. They do not go beyond general suggestions and have not resulted in an agriculturally valid method for the said purposes. Nor do they describe an apparatus that can be used industrially for treatment of seeds in a controlled way and with an adequate production.

It is therefore a purpose of this invention to provide a method for accelerating the germination of seeds and promoting the growth of crops by the irradiation of the seeds.

It is another purpose of this invention to provide such a method that will provide the desired results with practically every kind of seeds.

It is a further purpose of the invention to provide such a method that is efficiently applicable on a productive agricultural scale.

It is a further purpose of this invention to provide an apparatus for carrying out the method of the invention on an industrial scale.

It is a still further purpose of this invention to provide such an apparatus which comprises means for controlling the relevant process parameters.

It is a still further purpose of this invention to achieve the aforementioned purposes at a limited cost, and with the light sources that are commercially available.

Other purposes and advantages of the invention will appear as the description proceeds.

SUMMARY OF THE INVENTION

According to the invention, the seeds to be treated are irradiated with radiation that is a simulation of the solar visible spectrum, viz., that approximates the solar spectrum in the visible range of wavelengths, which, as is known, is approximately from 400 to 700 nm. Suitable sources of such radiation are Xenon lamps. The light produced by the chosen lamps may have the desired spectrum. If not, filter means should be provided for filtering of IR and UV light. The presence of the filter means is desirable in any case in a pilot apparatus for the evaluation of the light sources and for the adjustment of process parameters to various types of seeds, but may be undesirable in an apparatus for continuous, high production.

The irradiating light is pulsed at a frequency that goes from about 10 to 150 pulses per minute, e.g., about 60 pulses per minute. The pulses are separated by intervals of no radiation, the length of which is preferably comprised between 10 and 90% of the duration of the pulses, and is preferably equal to the duration of the pulses. The seeds are cooled during the process, viz., during the radiation pulses and between them. Preferably they are cooled by means of a stream of gas, e.g., air.

As has been said, the solar simulation is preferably produced by means of xenon lamps. When a filter is used, the infrared portion of the radiation, if it comprises a substantial amount in the 800/1100 nm region, is preferably filtered off by means of a water filter. The ultraviolet radiation is filtered off by means of any known type of UV filter, such as are well known in the art.

Preferably, according to the invention, the seeds are subjected them to irradiance from 5,000 to 35,000 W/sqmt, e.g., 20,000 W/sqmt, for a period from 30 to 900 seconds, e.g., 180 seconds. The optimal radiation dose, irradiance and time of irradiation will depend on the type of seed, its shape, color, size, weight, thickness of shell and density, the volume of the individual seeds and the compactness of the seed bed, viz., the weight of seed per square meter of the fluidized seed bed. The temperature should at no time exceed 35° C. in the seeds, to avoid damage thereto.

The invention further comprises an apparatus which comprises a solar simulator, means for exposing the seeds to radiation pulses, means for cooling the irradiated seeds and means for impelling the seeds to travel through the apparatus.

The means for exposing the seeds to radiation pulses may comprise means for activating the solar simulator or simulators by pulses, or screen means for intermittently intercepting the radiation, or mechanical or optical means for intermittently exposing the seeds to the radiation, or a mechanical or optical deviator device for deviating the radiation intermittently to different paths or portions of the seeds. In a preferred form of the invention, the radiation produced by a plurality of solar simulators is concentrated in a fixed region, and the seeds are caused to traverse said region repeatedly for short times, each such passage being equivalent to a radiation pulse.

The means for impelling the seeds to travel through the apparatus should be controllable, so to vary—other things being equal—the number of radiation pulses, their duration, the intervals between them and the overall amount of radiation directed on the seeds.

A preferred form of the apparatus according to the invention comprises a drum along which the seeds travel, a funnel or other feeder being provided to feed the seeds into the cylinder and a discharge at the end of the cylinder opposite to the feed. The drum is rotatable and is defined, in a preferred embodiment, by a plurality of longitudinal ribs and by a permeable sheath, e.g., made of netting, stretched over said ribs. The ribs engage the seeds, as the drum rotates, lift them from a lowermost position to an uppermost position, and let them fall when they reach this latter between guide surfaces, whereby they form a vertical layer. The permeable sheath permits the passage of a cooling gas, preferably air. Said structure of the drum, however, is not unique and could be substituted by a different structure, as long as this comprises means for entraining the seeds and apertures for the passage of a cooling gas. An elongated stationary structure, coaxial with the rotatable cylinder and of approximately the same length, hereinafter called "envelope," supports a plurality of light sources, preferably rod-like, axially oriented, Xenon lamps, and mirror surfaces so shaped as to concentrate the light of the lamps into a narrow axial strip, wherein the envelope is apertured to expose the falling seeds to the concentrated light. Air blower means is provided for blowing air from the discharge end of the cylinder to the feed end thereof, whereby to cool the seeds and exchange the air inside the machine. Rotatable cylinder and stationary drums are housed in a frame, which is provided with adjustable supports to permit to vary the slant of the drum and therefore the speed at which the seeds traverse it. Motor and control means and a power source are provided as required for the operation of the machine.

In another embodiment, feed means, such as a hopper or any convenient mechanism, feeds the seeds onto the top of the drum, and the drum raises them and carries them through an arc of its rotation, where they are exposed to radiation for a short time. The seeds are advanced longitudinally, viz., in a direction generally parallel to the axis of the drum, from their feed to a discharge by any convenient means that will be described, therefore the seeds are exposed to radiation repeatedly and each time for a short time at each turn of the drum rotation. Each such exposure constitutes a pulse of the radiation. A plurality of light sources, preferably rod-like, axially oriented, Xenon lamps, are mounted above the drum, and mirror surfaces are provided, so shaped as to concentrate the light of the lamps on the seeds retained at the top of the drum over a predetermined arc of said drum. The longitudinal advancement of the seeds is preferably caused in part by the fact that the drum is set at a small angle to the horizontal, being slightly higher at the feed end and lower at the discharge end. A cooling gas is preferably impelled to flow over the periphery of the drum and is preferably so directed as to cooperate to the advancement of the seeds.

In other embodiments of the invention, the seeds are advanced through the machine by mechanical or pneumatic conveyor means, so that they form two (or more) parallel strips of seed layers on one conveyor or on two (or more) parallel conveyors, and an irradiating light beam, optionally filtered, is directed alternatively to each of the two (or more) strips, whereby to produce a pulsed radiation.

DETAILED DESCRIPTION OF PREFERRED EMBODIMENTS

Figure 1:
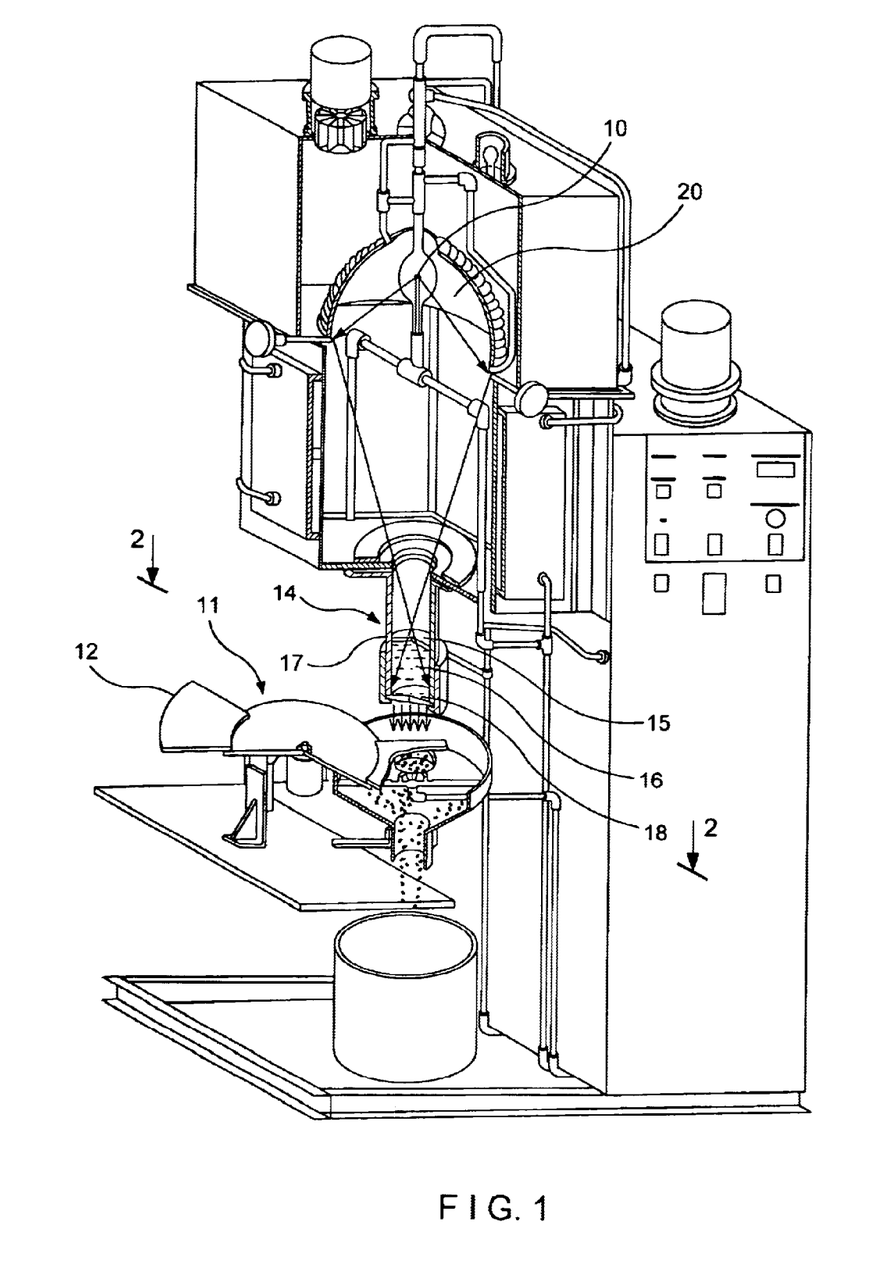
FIG. 1 is a schematic perspective view, partly in cross-section, of an apparatus illustrating the principle of the invention.
Figure 2:
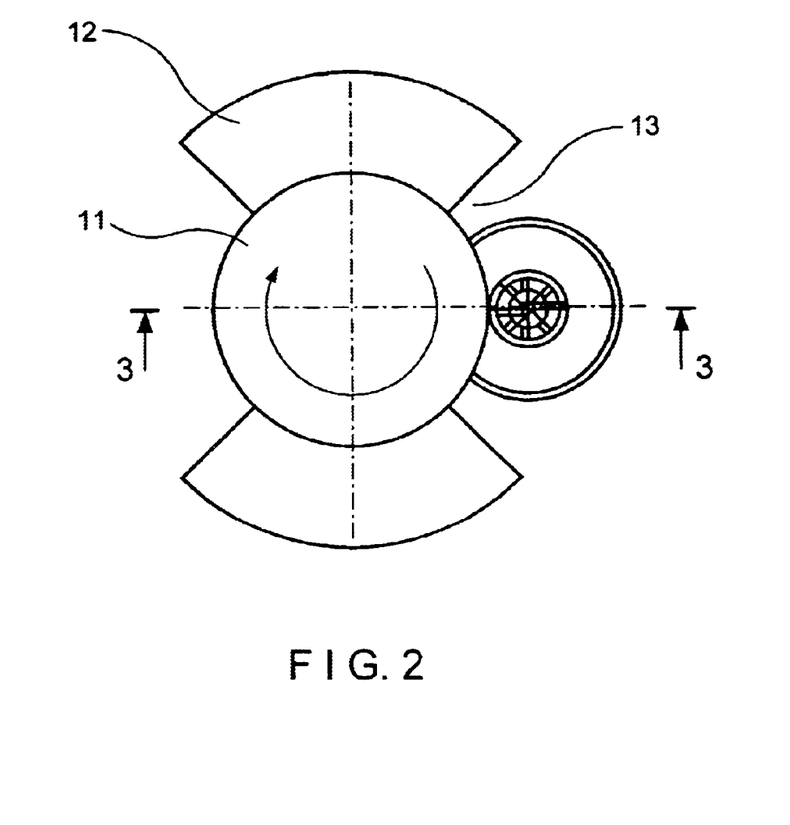
FIG. 2 is a cross-section of the apparatus of FIG. 1 along the plane II—II of FIG. 1. looking downwards.

With reference now to FIGS. 1 to 3, numeral 10 generally designates a source of light which constitutes a solar simulation, for instance, produced by Oriel Corporation, Stratford, Conn., USA. The solar simulation apparatus does not require any detailed description, as it is well known and commercially available. In the embodiment of FIG. 1, the solar simulation source is surrounded by a semispherical mirror 20, which directed the light downwards. The light is periodically interrupted, to produce pulses, by means of a rotating screen disk 11, seen in plan view in FIG. 2, which is constituted by a number (in this example, 2) of equal sectors 12 separated by gaps 13 having the same shape and size of the sectors. The light passes through gaps 13 when these cross the path of the light beam in the rotation of the screen disk, but when a sector 12 crosses said path, the light is intercepted. In this way a pulsed light radiation is produced below screen disk 11, with a pulse frequency mn/sec and a duration of each pulse of ½ mn/sec, if m is the number of sectors and n is the number of turns of the screen disk per second. Thus, if the screen disk 11 is rotated at a speed of 10 turns per second, the light below it will have 20 pulses per second, each lasting a 40th of a second, separated by 20 intervals per second of the same duration.

Above screen disk 11, and before being pulsed, the light produced by solar simulator 10 is filtered, in this embodiment, by an ultraviolet/infrared filter, generally indicated at 14. The filter, however, can be missing, particularly in apparatus for continuous industrial production, if the solar simulator already emits light having the desired wavelength distribution. The light reflected by mirror 20 is focused on top opening of filter 14. The same result, however, could be achieved by a different optical system. Filter 14 may have any structure, as long as it is adapted to effect the desired wavelength filtration, but in this embodiment it comprises a disk 15, transparent to visible light but adapted to intercept ultraviolet light, and a body of water 16 which filters the infrared light, contained in a cylindrical container 17, the bottom 18 of which at least is transparent. As a result, the light beam below filter 14 will have a spectrum ranging approximately from 400 to 700 nm. The light beam, when it passes through the openings 13 of disk 11, impinges onto a bed of seeds 21 (see FIG. 3), supported by a support 22, constituted by a net or similarly apertured plate or sheet and mounted in a container 27. A current of air, schematically indicated at 23, is conveyed through the support 22 and the seed bed 21 by an impeller or other suitable device, and cools and mixes the seeds and concurrently lifts them to form a fluidized bed. The seeds are thus submitted to the dose of radiation required by the particular seeds being treated. Since the apparatus operates in batches, the treated seeds can be intermittently discharged, e.g., into container 28 through a hopper 29.

Figure 3:
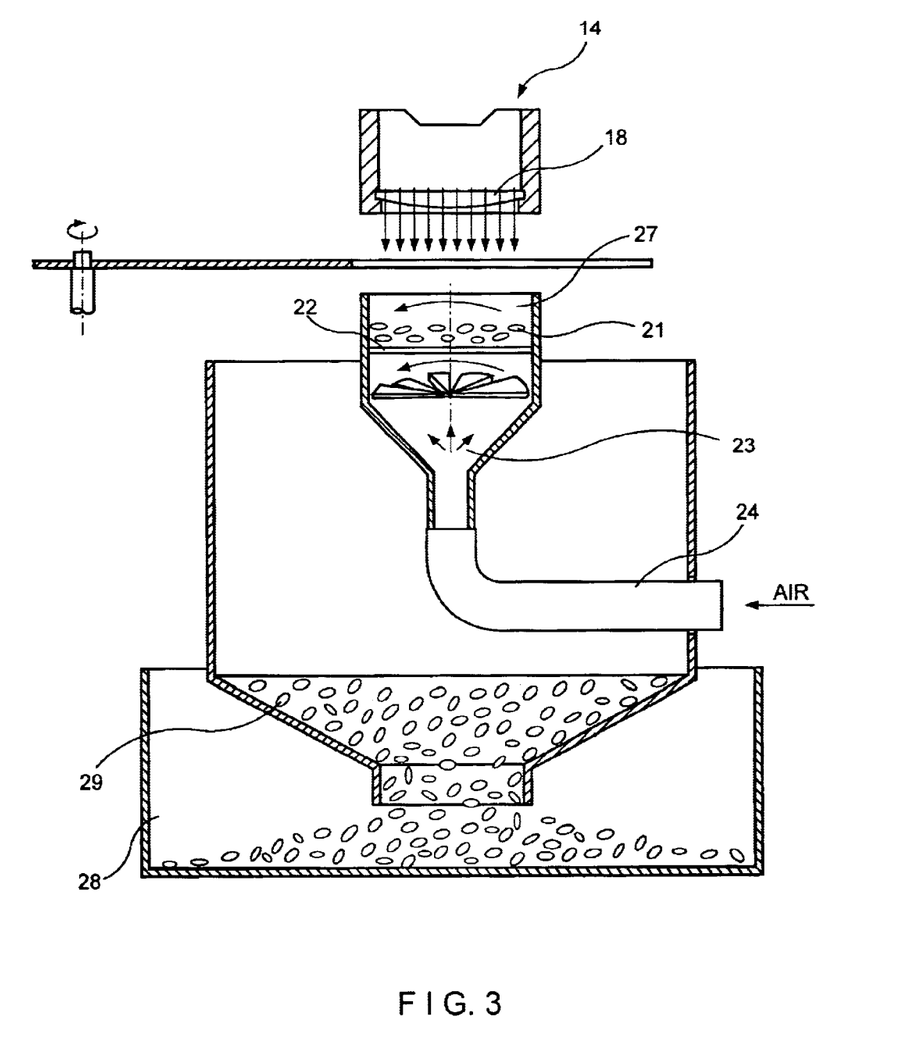
FIG. 3 is a cross-section of the lower part of the apparatus taken on the plane III—III of FIG. 2.
Figure 4:
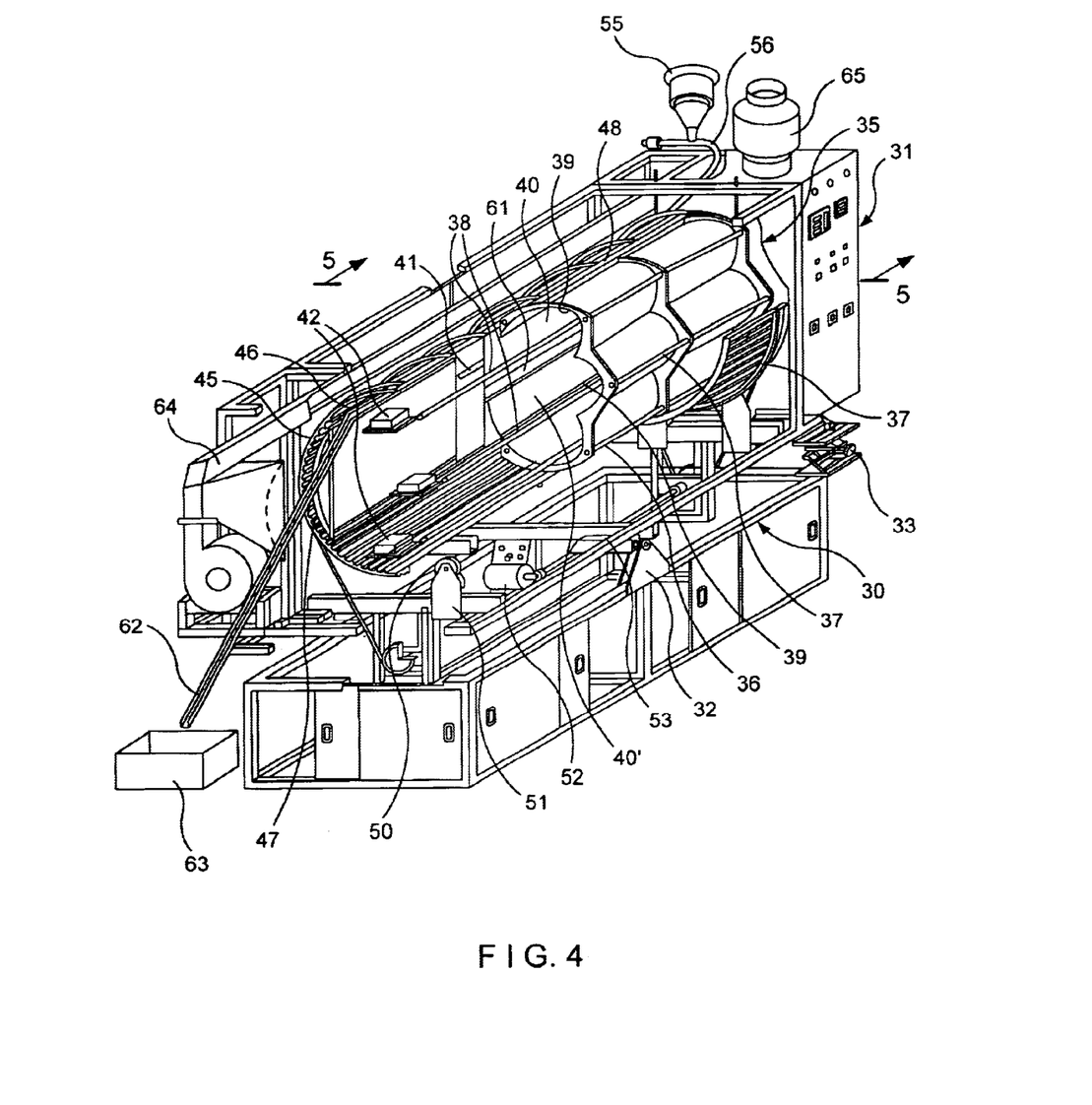
FIG. 4 is a schematic perspective view, partly broken off, of an industrial apparatus embodying an embodiment of the invention.
Figure 5:
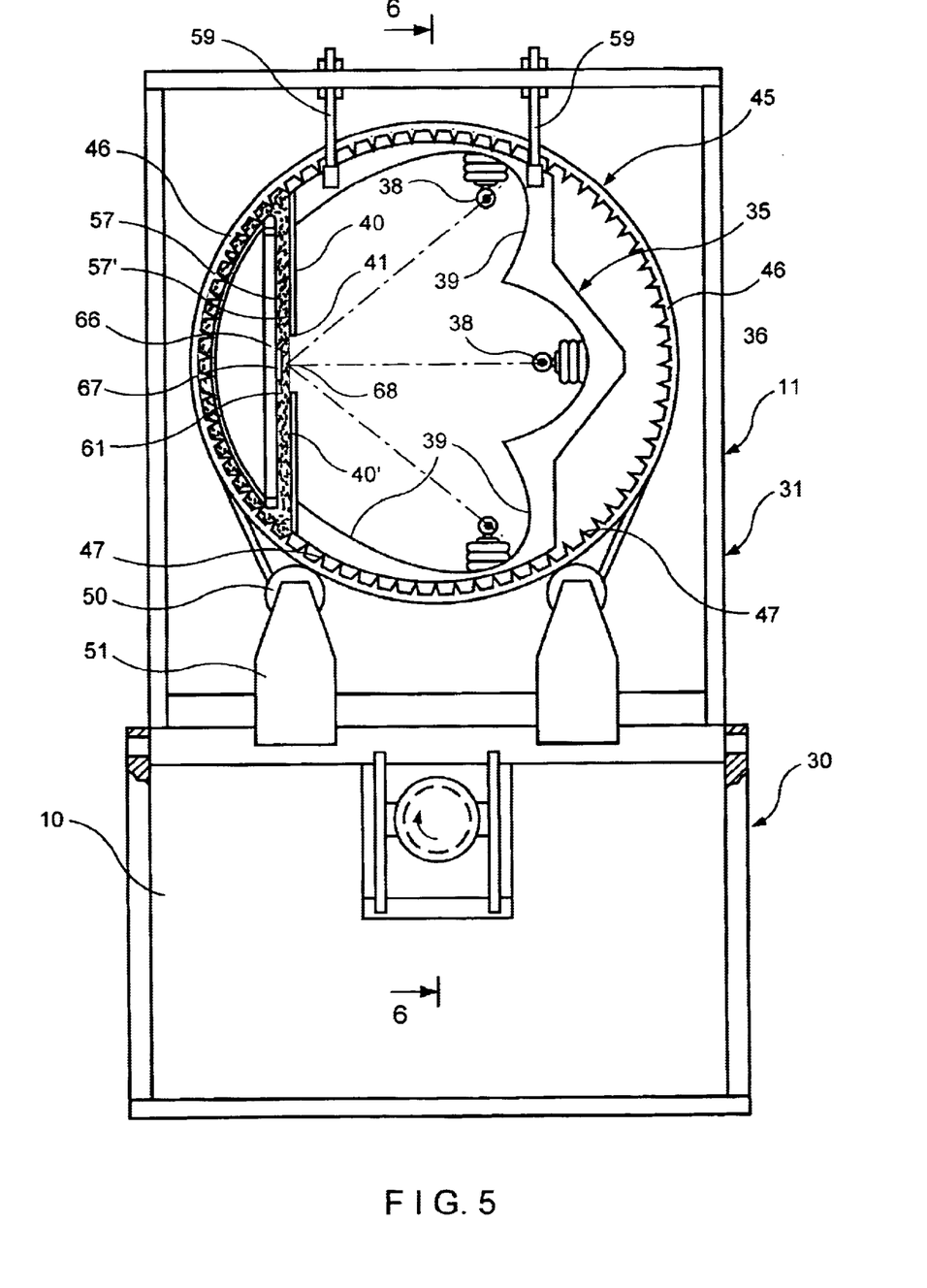
FIG. 5 is a vertical, transverse cross-section of the apparatus of FIG. 4, taken on plane V—V of FIG. 4.
Figure 6:
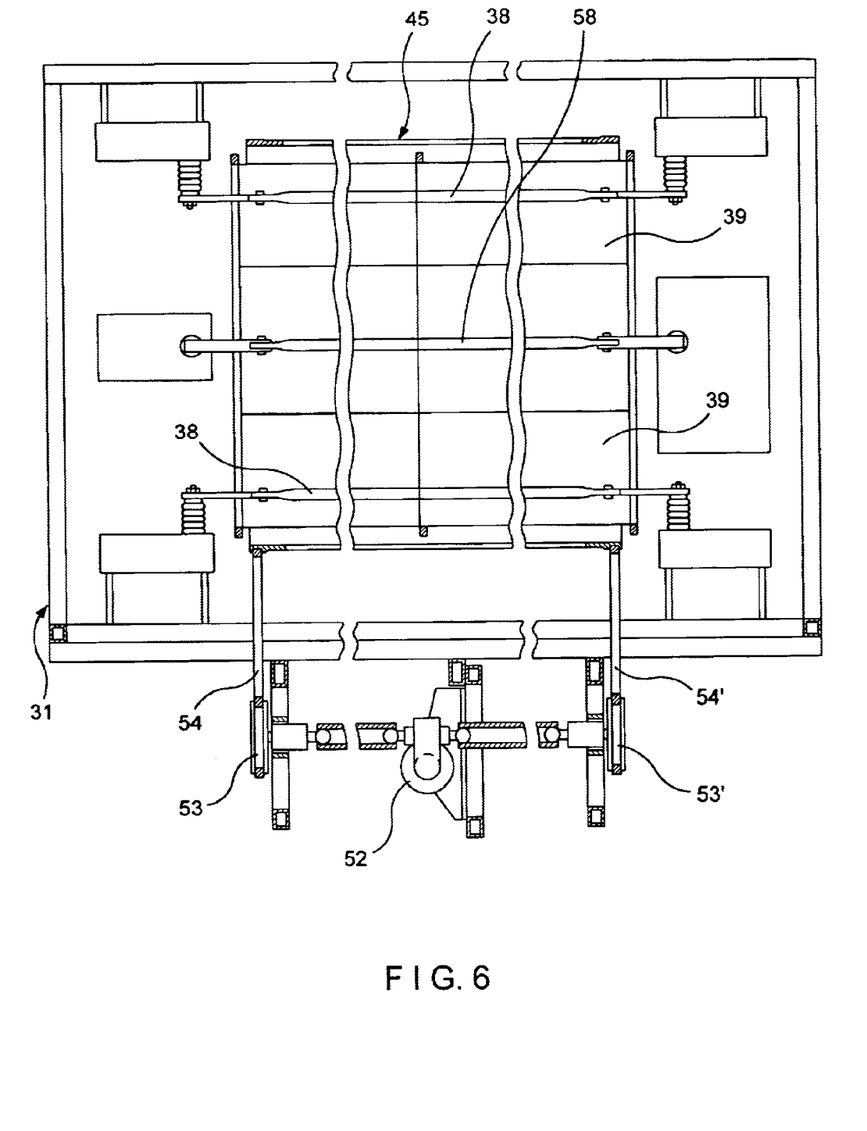
FIG. 6 is a vertical, longitudinal cross-section of the apparatus of FIG. 4, taken on plane VI—VI of FIG. 5.

The apparatus of FIGS. 1 to 3 will only treat a small batch of seeds at a time, and is therefore mainly a pilot equipment, which may be used for determining the parameters of an industrial process for each type of seed. Preferred industrial machine is illustrated in FIGS. 4 to 6.

Said machine is provided with a base generally indicated at 30, on which is supported a casing generally indicated at 31. The casing 31 is pivotedly supported on base 30 at a central or rear point or points of its length by means of pivot supports 32, and at a front point of its lengths and rests on adjustable supports 33. The words "front" and "rear" refer to the path of the seeds, viz, respectively to the zone in which the seeds are loaded into the machine (at the right side of FIG. 4) and the zone in which they are discharged therefrom (at the left side of FIG. 4). By adjusting supports 33 to make them higher or lower (by means not shown, as they may be conventional), casing 31 can become angularly displaced, with respect to base 30, by rotation about pivot supports 32, thereby changing its slant, for the purpose which will be explained.

Casing 31 supports a stationary envelope, generally indicated at 35, which comprises a number of transverse frames 36 connected by longitudinal rods 37. Frames 36 may be suspended from casing 31 by means of ties 59 (see FIG. 5) or in any other suitable way. Longitudinal lamps 38, which provide the required irradiation, are mounted in any convenient way on casing 31.

Transverse frames 36 support concave mirrors 39. In the embodiment shown, there are three lamps 38, activated by switches 42, and three concave mirrors 39, but this number could be changed. Two fixed vertical plates 40–40' are supported by frames 36. Plates 40 and 40' are spaced to define a longitudinal gap 41.

Casing 31 also supports a rotary drum, generally indicated at 45. More precisely, rotary drum 45 comprises transverse, circular ribs 46, connected to longitudinal ribs 47, over which is stretched a net 48, or a sheet of apertured and air-permeable material. Ribs 46 rest on rollers 50, rotatably mounted on supports 51, so that drum 45 may freely rotate. A motor 52 sets the drum into rotation wheels 53–53' and belts 54—54.

The seeds to be treated are fed by means of a funnel 55. From said funnel, through a conduit 56, they fall into the drum at the upper or front end thereof. As the drum rotates, the longitudinal ribs 47 lift the seeds until they reach approximately the top of the drum. Therefrom they fall, forming a vertical layer 61 between plates 40–40' and a guide plate 66 (see FIG. 5). Two adjustable, preferably angularly adjustable, slats or other elongated elements 57–57' are provided between said plates 40–40' and said guide plate 66, to control the fall of the seeds and its speed, so as to adjust the period of time during which the seeds are exposed to the radiation. The mirrors 39 are so shaped as to concentrate the radiation of all the lamps at a focus 68 in the gap 41 between the two plates 40 and 40', as shown in FIG. 5. A mirror 67 is mounted in front of the focus 68 to reflect the radiation though the seed layer 61. The seeds, in their fall, are screened by plates 40 and 40' from the radiation until they pass in front of the gap 41, where they receive the concentrated radiation of all the lamps.

Due to the slant of the drum, the seeds proceed from its upper or front end to its lower or rear end, while they are continuously brought by ribs 47 from a lowermost position to an uppermost position, fall down from said uppermost position, and receive a pulse of radiation as they pass in front of gap 41. Finally, they reach an uppermost position at the rear end of the drum, and fall through a slide 62 into a receiving container, schematically indicated at 63. Concurrently the seeds, as they travel from the front to the rear of the drum, are cooled by gas, generally air, which is supplied by blower 64, placed near the rear end of the apparatus. The gas exits the apparatus from an outlet 65 at its front end. It is seen that the gas flows essentially in countercurrent to the direction in which the seeds advance longitudinally along the machine, or, in other words, approximately in a direction opposite to the longitudinal component of the seeds' motion. The gas stream, besides cooling the seeds, contributes to maintain the atmosphere within the apparatus in a sufficiently pure condition, removing the moisture that is emitted from the seeds due to the irradiation and gases such as ozone that may be produced by the radiation.

The amount of radiation which the seeds receive depends obviously on the intensity of the radiation produced by the lamps and concentrated onto gap 41, on the width of said gap, the speed by which the seeds fall, the rotary speed of the drum, and the speed by which the seeds travel longitudinally along the machine. All these factors are controlled by appropriately designing the components of the device, by adjusting the slant of casing 31, and by controlling the operation of all components by electronic means, easily provided by the skilled person and therefore not particularly described. Each seed will require an appropriate control of the machine.

It will be understood that in the machine hereinbefore described the seeds receive a pulsed irradiation, but not because the lamps themselves are pulsed, but because the seeds are screened from the radiation except for brief, intermittent periods of time. However, it will be evident that the radiation could be so shifted by optical means as to impinge on any given seed only with the desired pulsing frequency and pulse and interval duration, as long as those variables are within the general limits set forth by the invention. Further, the invention could be carried out in different mechanical way: e.g., the seeds could be carried by different mechanical means than those of the embodiment illustrated, for example, by belt conveyors or the like.

In the machine of the embodiment described, the following mechanical and electrical features preferably obtain. The slant of frame 35 is from zero to 15°; the speed of the rotation of the drum is from 0.2 to 2.0 rpm; the width of gap 41 through which the seeds are exposed to radiation is from 450 to 189 mm. A type of Xenon lamp used is, e.g., Arc XE Tube (Axt 20) produced by Oriel Corporation.

Figure 7:
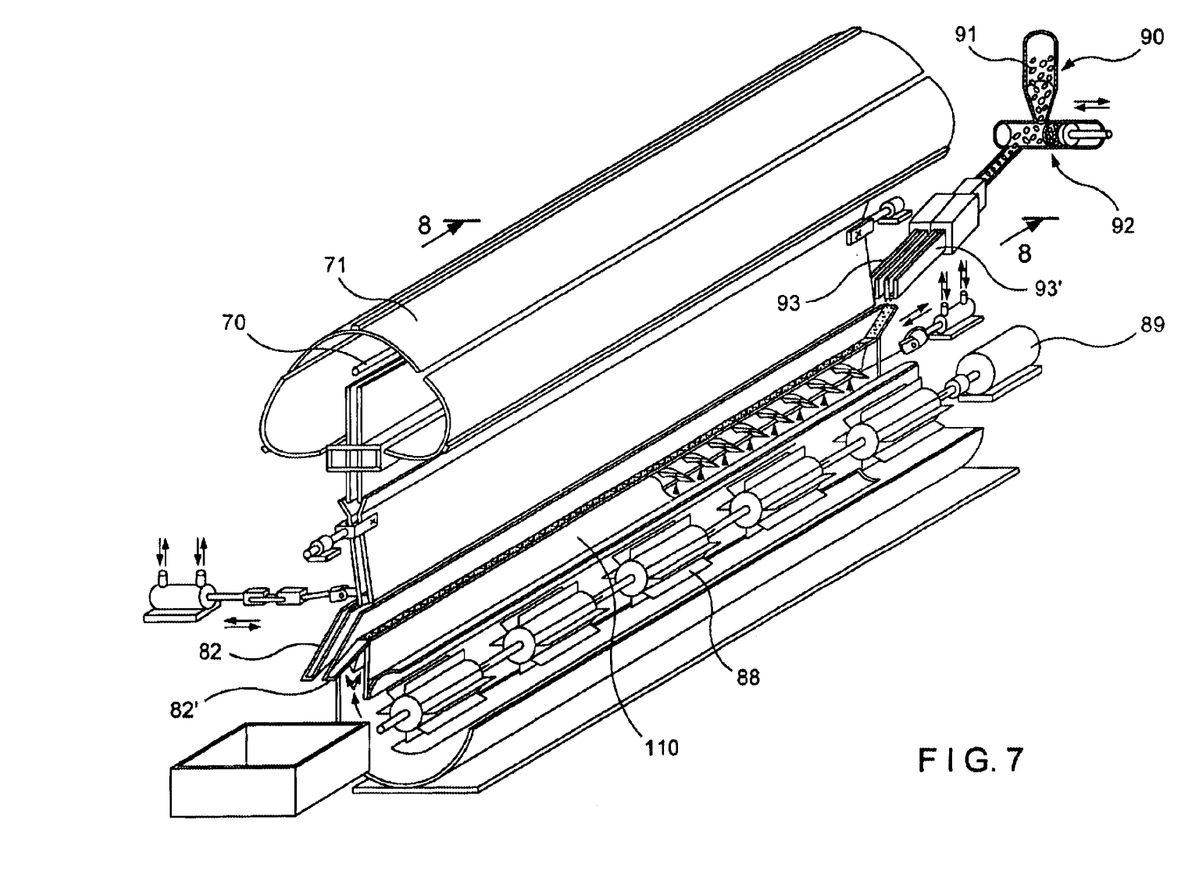
FIG. 7 is a schematic perspective view of an industrial apparatus embodying another embodiment of the invention.
Figure 8:
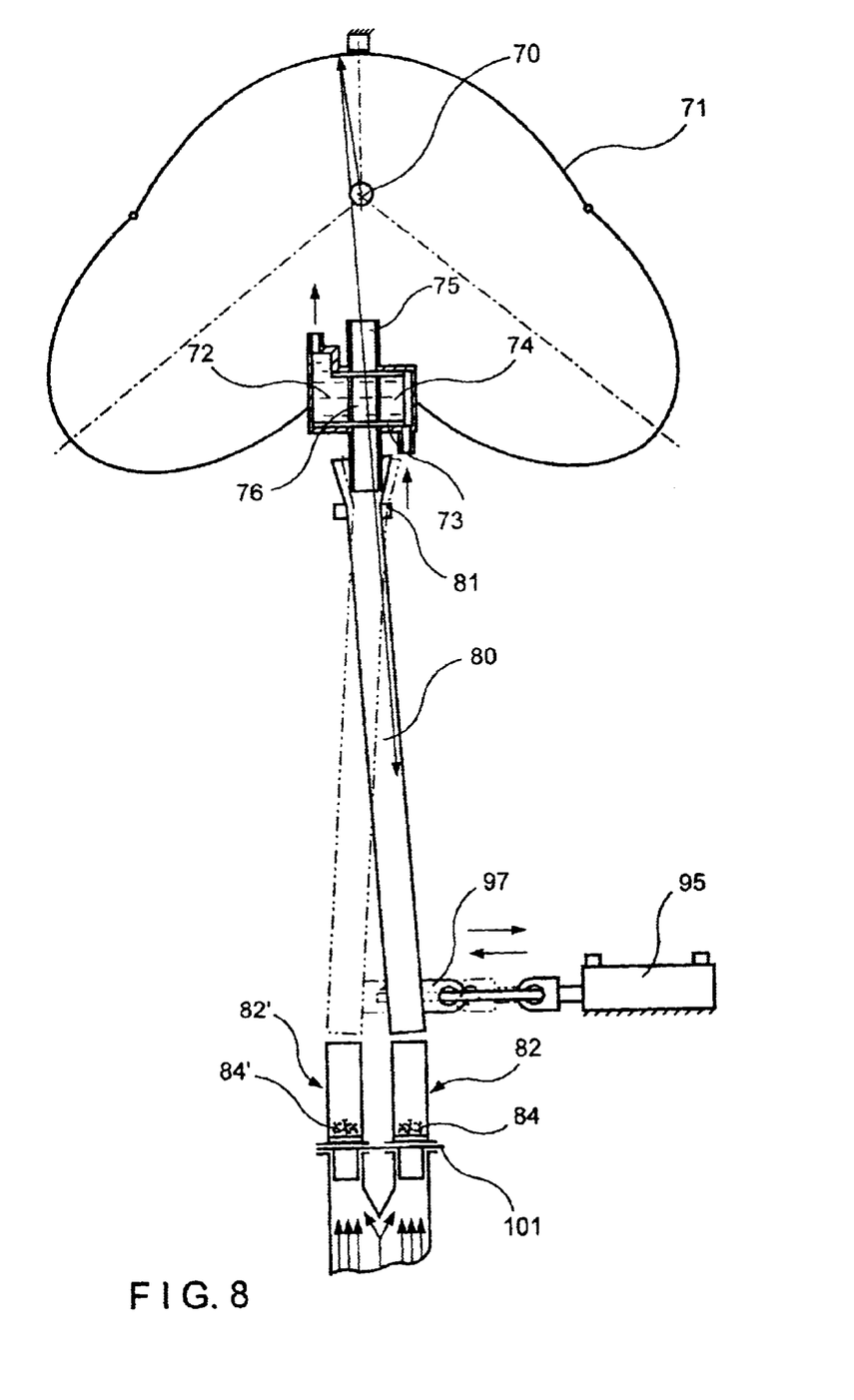
FIG. 8 is a vertical, transverse cross-section of the apparatus of FIG. 7, taken on plane VIII—VIII of FIG. 7.
Figure 9:
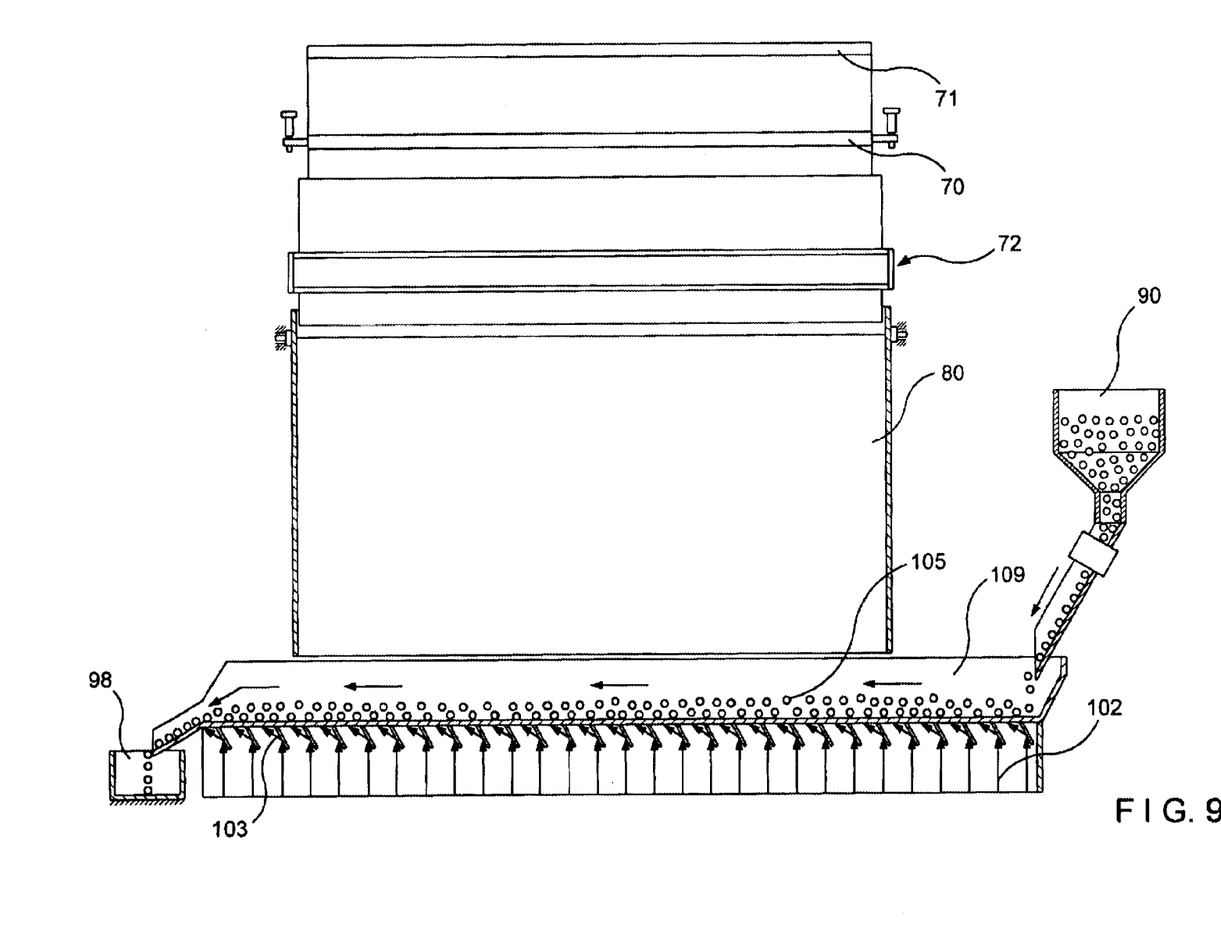
FIG. 9 is a longitudinal cross-section of the apparatus of FIG. 7, taken on an axial

An alternative embodiment is illustrated in FIGS. 7 to 9. Herein, the solar simulator 70 is elongated and its length determines the length of the irradiated zone of the machine. The light can be pulsed by a mechanical intercepting device, based on the same principle as the sector screen disk of the embodiment of FIGS. 1 to 3, but differently shaped to conform to the shape of the solar simulator 70. However, in this embodiment a different pulse-generating system has been adopted, as will be explained hereinafter.

The light issuing from the solar simulator 70 is reflected by a reflector 71 and passes through a filter 72. Filter 72 could be missing, if solar simulator 70 already provided the desired light spectrum. A narrow blade of light directed parallel to the direction of motion of the conveyors, hereinafter described, is thus produced. Filter 72 comprises an ultraviolet filter 73 and a body of water 74 contained in a portion 76 of the filter. Since the apparatus operates continuously, the body of water 74 would tend to become heated, and therefore cooling means should be provided, e.g., a stream of cooling water is passed in portion 76. However, different cooling means could be employed.

In this embodiment, two conveyors 82 and 82', parallel and close to one another, and having seed supporting surfaces made of nets or other material provided with apertures for the passage of air, form two elongated beds or strips of seeds, as indicated at 84 and 84' in FIG. 8. The filtered light is channeled by an elongated sleeve 80, pivoted at 81 for limited angular displacement, between two positions (see FIG. 8, in which one position is indicated in full lines and other in broken lines) in one of which it directs the light beam onto seed strip 84 and in the other of which it directs the light beam onto seed strip 84'. Each seed bed is therefore alternatively irradiated. The overall radiation time is determined by the length of the irradiated zone and the speed of the conveyors and is obviously one half of what it would be if the radiation impinged constantly on one seed bed. An arrangement of impellers (generally designated 88) directs air to below and through the conveyors and the seed beds, actuated by motor 89. Means for loading the seeds (generally designated 90) schematically comprise a hopper 91, an intermediate conveyor 92, and loading chutes 93–93' for conveyors 82–82'. The deviation of the light from one conveyor to the other could also be produced by optical means, such as mirrors, prisms or the like.

In the embodiment illustrated in FIGS. 7 to 9, the seeds are carried by one or more conveyors. The seeds are loaded either onto a continuous conveyor, which may have an axial longitudinal partition dividing it into two equal halves, or—as in this embodiment—onto two equal, parallel, adjacent conveyors 82 and 82'. The conveyors may be belt conveyors and be actuated continuously. However, in this embodiment, the conveyors are pneumatic conveyors. The conveyors, whatever their structure, are pervious to air. Each comprises a horizontal or slanted, air-pervious plate 101 on which the seeds are loaded and along which they are advanced by the vibration of the conveyors produced by motor 95, while they are fluidized and cooled by a stream of air produced by impellers 88. FIG. 9 illustrates how the conveyors operate. The stream of air generated by the impellers is indicated by vertical arrows 102. Deviator blades 103 impart to the air a direction slanted towards the discharge end of the conveyor. The combination of vibration and pneumatic action causes the seed beds 105 to advance along the conveyor. Side plates such as 109 and 110 prevent the seeds from spilling outside the conveyor in the processing zone of the machine. The seeds are loaded by the loading system 90 (see FIG. 7) uniformly over the surface of the conveyor, if a single conveyor is provided, or onto the two adjacent conveyors, always in such a way that two adjacent and parallel beds of seeds are produced. The radiation is shifted from one bed to the other by angularly shifting the tube 80 from the position indicated in full lines on FIG. 8 to that indicated in broken lines, and vice versa. The angular shift may be produced by any suitable means, in this embodiment by a motor 96 imparting a reciprocating motion to a connecting rod 97. As has been said, it could be produced by optical means, e.g., by a mirror that can be shifted between two different angles: depending on the angle at which the mirror is set, the light will impinge upon one or the other of the seed beds. It is clear that each seed granule will be irradiated in a pulsed manner, with the desired frequency and length of pulses. The seeds are discharged at 98, after having received the required treatment.

In another embodiment of the invention, for example, the solar simulator may have a power supply of 4–20–60 kW, the mirror 36 is actuated so as to produce 10–75 pulses per minute, having a duration of 0.1–0.9 sec. each, separated by intervals of 0.1–0.6 sec. each, and the seeds are advanced under the radiation at a linear speed of 0.1–1.0 meters per minute, so that the seeds are irradiated for a total time of 30–90 seconds.

Figure 10:
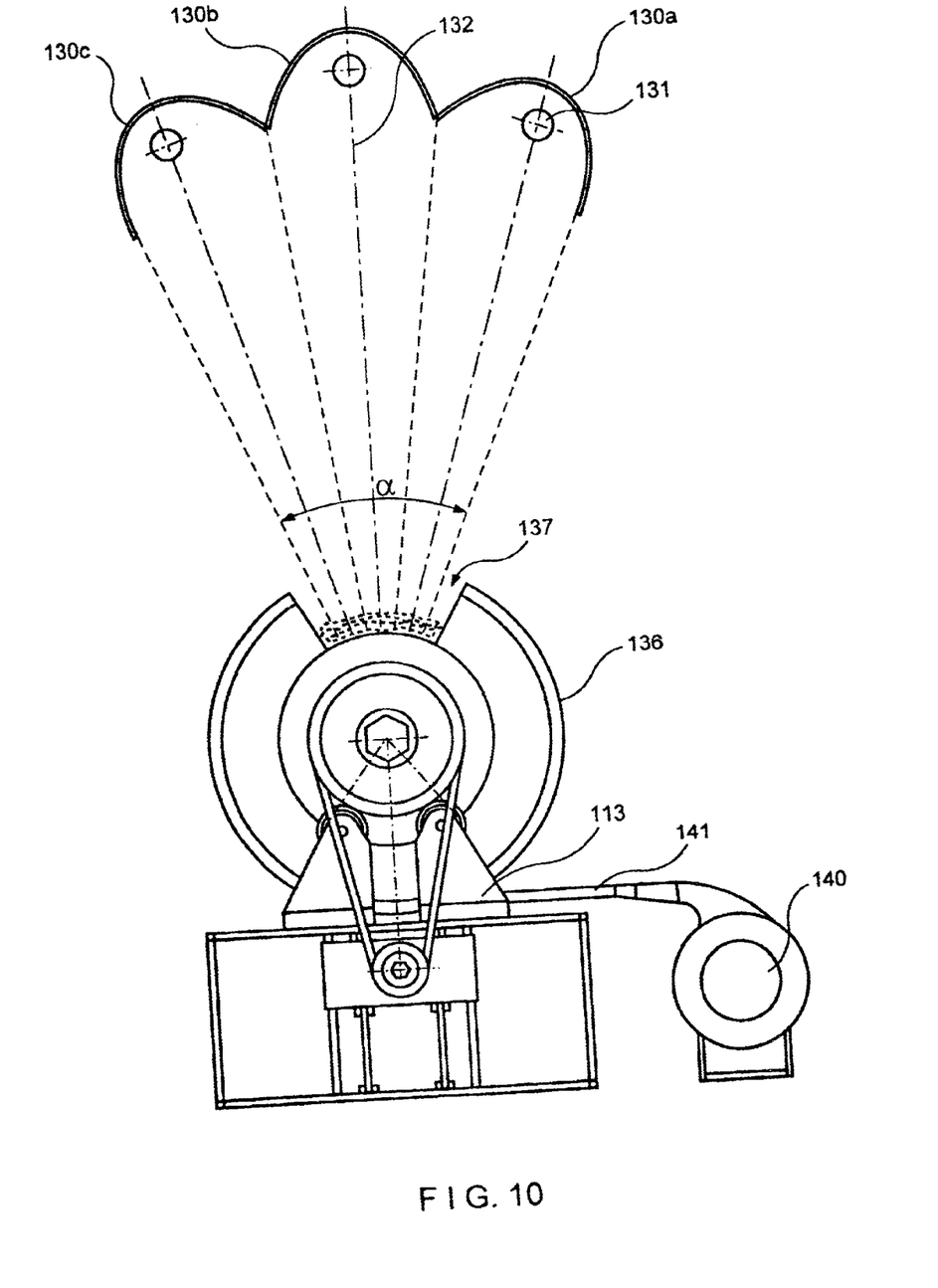
FIG. 10 is a schematic vertical end view of an industrial apparatus according to still another embodiment of the invention.
Figure 11:
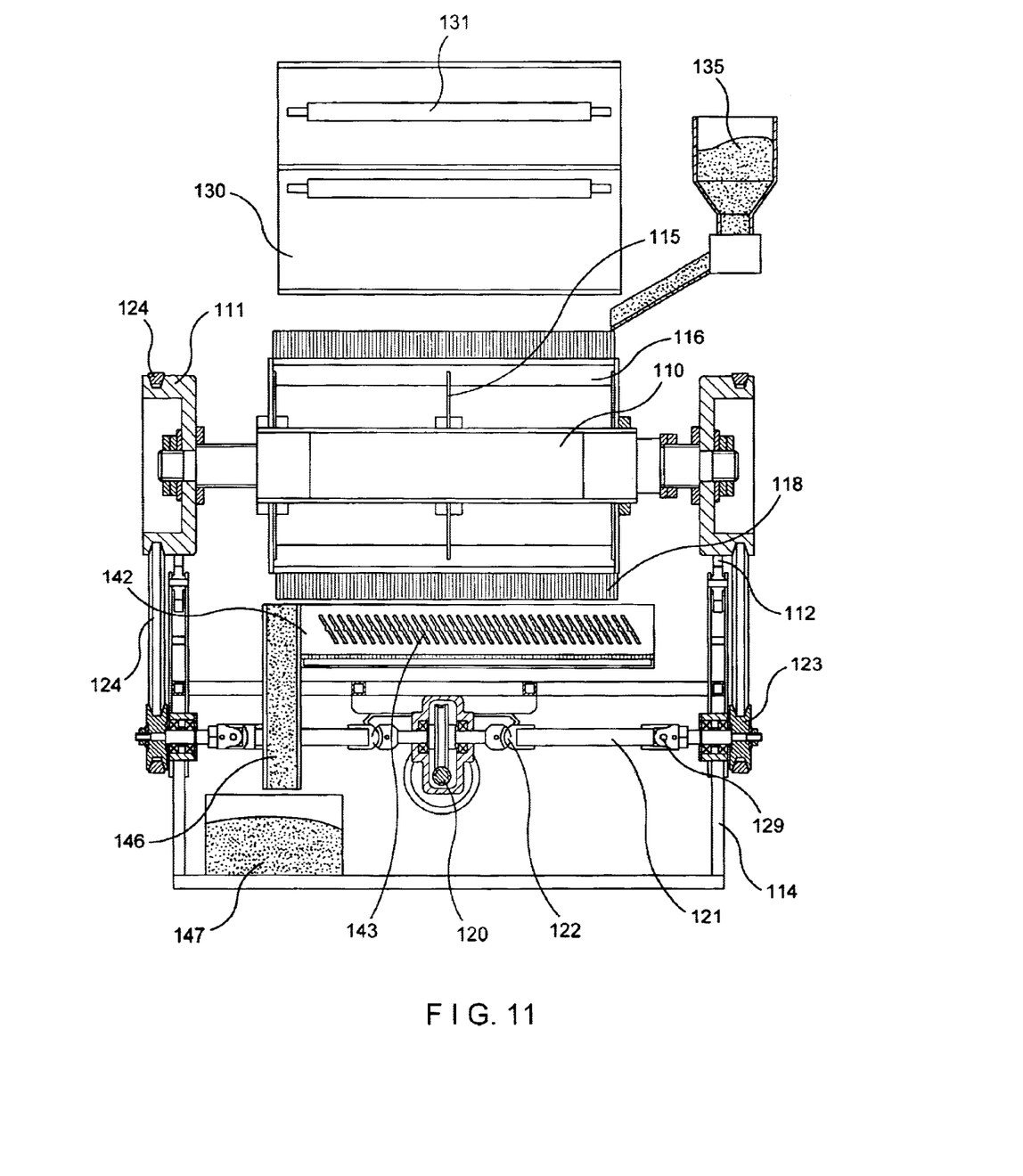
FIG. 11 is a schematic vertical side view of the apparatus of FIG. 10.
Figure 12:
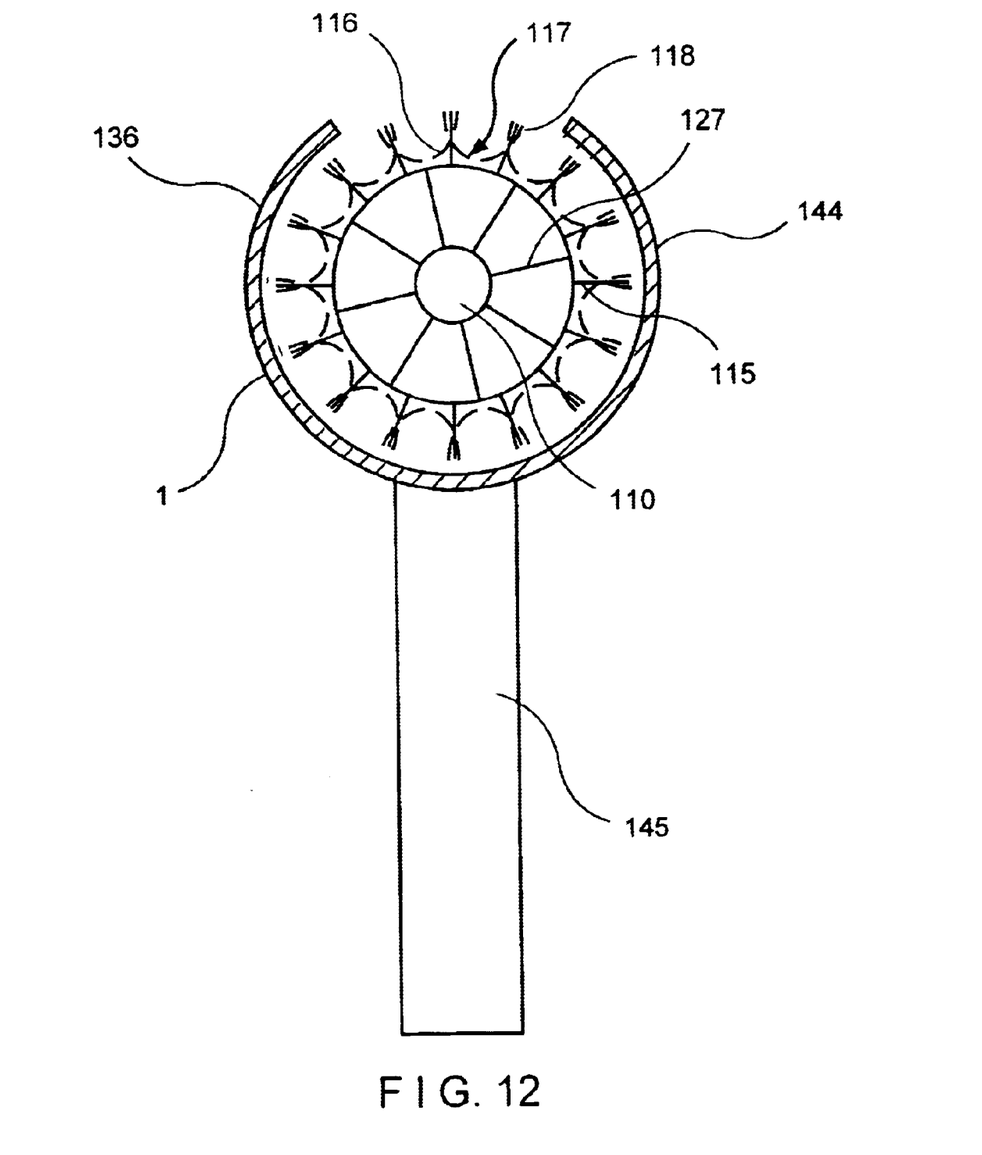
FIG. 12 is a schematic transverse cross-section of the drum

In the embodiment of FIGS. 10 to 12, a shaft 110 carries at its ends cups 111 which are supported each by a roller 112 mounted on a leg 113 supported and solid with a base 114. Shaft 110 has keyed thereto spokes (round plates) 120, which connect said shaft 110 to a cylindrical shell 127. Said shell 130, in turn, carries round ribs 115 which support a net 116. As shown in the detail of FIG. 12, net 116 sags between consecutive ribs 115, forming pockets 117. Ribs 115 also carry at their tips flexible projections, which form a brush-like element 118 on each rib. The radial plates 127 could be omitted by attaching longer ribs directly to the shaft 110. In this case, however, shaft 110 should have a greater diameter, to avoid creating pockets 117 that are too deep.

A longitudinal shaft 120 actuates two transverse shafts 121 through two universal joints 122. Each transverse shaft 122 actuates a pulley 123 keyed to it. A belt (a trapezoidal belt in the embodiment illustrated) is mounted on each pulley 123 and on each drum 111. Therefore, when longitudinal shaft 120 is rotated by motor and drive means, not illustrated as they can be conventional, shaft 110 is also rotated through shafts 121, pulleys 123 and belts 124.

The assembly of the shaft 110, ribs 115, net 116, and (when present) radial plates 120 and cylindrical shell 127, will be referred to as "drum," though it is not a solid body and has no cylindrical outer surface, because said assembly functions as a drum and could be replaced by a conveniently shaped drum.

An assembly of reflectors 130 and light sources 131 is supported in fixed position above the drum by support means, not illustrated as they can have any convenient configuration. In the embodiment illustrated, the light sources are rod-shaped Xenon lamps, each located at a central point of the space bounded by a reflector 130. The reflectors are not parabolic, because they are not intended to reflect the light of sources 131 as a sheaf of parallel beams, but in the embodiment illustrated they reflect said light uniformly onto an arc of the drum indicated in FIG. 10 by α. Said arc is chosen depending on the desired duration of the radiation pulses, which generally varies from 0.1 to 0.9 sec. For example, if the rotary speed of the drum is one turn per second, a pulse duration of ⅛ sec will be obtained by making =45°. The frequency of the pulses, on the other hand, will depend of the rotary speed of the drum only. The reflectors 130 situated at the sides (in FIG. 10, reflectors 130a and 130c) are preferably somewhat longer at their outer edges, as seen in the figure, to avoid dispersion of radiation.

The drum is housed in a casing 136, not shown in FIG. 11 so as to simplify the drawing, parallel to shaft 110. Said casing 136 is open at the top, as shown at 137, so as to permit the passage of radiation reflected by reflectors 130. The aperture 137 should extend through an angle slightly longer then α. The seeds are fed by hopper 135 or other feed means into housing 136. They may be fed directly onto the drum or not, as long as they fall into housing 136. They accumulate at the bottom of said housing, and are lifted by ribs 115 and net 116, at each turn of the drum, to reach the top of the drum, opposite to the aperture 137. As the drum turns, they fall back to the bottom of casing 136, only to be lifted again at the next turn. Meanwhile, they advance by gravity from the end of the casing, below the feed hopper 135 or other feed means, until they reach a point near the opposite end on the casing, which communicates with discharge conduit 146, through which the treated seeds exit from the apparatus, and are stored in container 147.

Means for feeding a current of gas, generally air, to the apparatus, are also provided. In the embodiment illustrated, said means comprise a blower 140, which feeds the air through a pipe 141 into a sleeve 142 of casing 136. In sleeve 142 are mounted slanted plates 143, which impart a longitudinal component to the direction of the air flow. Said longitudinal component is generally from the feed end to the discharge end of the apparatus, whereby the air current, besides having a cooling effect when cool enough, cooperates with the slant of the drum to drive the seeds through the apparatus. Preferably the slant of the plates 143 can be varied. Said slant, as well as the strength of the air current, determine the cooperation of said current to the speed of advancement of the seeds through the apparatus, and therefore to the duration of the treatment.

The parameters of the irradiation of the seeds can be controlled by controlling the speed of rotation of the drum, its diameter, the angle α, the slant of the drum with respect to the horizontal and the slant and intensity of the air supplied. The speed of rotation of the drum determines the frequency of the radiation pulses, the angle α determines their duration, and the slant of the drum and the slant and intensity of the air determine the duration of the treatment. Also, the type and power of the lamps, their number, their position, the shape, position and size of the reflectors, and the dimensions of the drum and the casing have an important influence on the treatment, but skilled persons can determine in each case all those variable as a function of the type and quantity of the seeds being treated, as well as of climatic conditions.

The following examples of effected treatments show the progress provided by the invention.

While some examples of the invention have been described by way of illustration, it will be apparent that the invention can be carried out with many modifications, variations and adaptations, without departing its spirit or exceeding the scope of the claims.

What is claimed is:

1. Apparatus for promoting by light irradiation the germination of seeds and the growth of plants generated by the seeds, which comprises:
   means for generating a light radiation that is a simulation of the solar visible spectrum;
   controllable means for impelling the seeds to travel through the apparatus;
   controllable means for applying to the seeds a number of radiation pulses of said light radiation; and
   means for controlling the duration of the radiation pulses and of the intervals between the radiation pulses.

2. Apparatus according to claim 1, further comprising a rotatable drum, having inner projections for engaging and entraining the seeds as the drum rotates from a bottom to a top position and apertures for the passage of a cooling gas.

3. Apparatus according to claim 2, wherein said travel of the seeds through the apparatus has a component of longitudinal advancement and further comprising air blower means for blowing air therethrough essentially in countercurrent to the seeds' longitudinal advancement, whereby to cool the seeds and exchange the air inside the apparatus.

4. Apparatus according to claim 3, comprising a casing housing the rotatable drum and provided with adjustable supports to permit adjustment of the slant of the drum and therefore the speed at which the seeds traverse the drum.

5. Apparatus according to claim 1, further comprising a rotary drum along which the seeds travel; a feeder for feeding the seeds into the drum near one end thereof; and a feed discharge at the end of the drum opposite to the feeder.

6. Apparatus according to claim 1, comprising a conveyor for conveying a seed bed through the apparatus.

7. Apparatus according to claim 6, wherein the conveyor is selected from the group consisting of belt conveyors and pneumatic conveyors.

8. Apparatus according to claim 1, wherein the controllable means for applying to the seeds a number of radiation pulses comprise means for activating a solar simulator by pulses.

9. Apparatus according to claim 1, wherein the controllable means for applying to the seeds a number of radiation pulses comprise a screen for intermittently intercepting the radiation.

10. Apparatus according to claim 1, wherein the seeds are located in at least one seed bed, and wherein the controllable means for applying to the seeds a number of radiation pulses comprise a deviator device selected from the group consisting of mechanical and optical deviator devices, for deviating the radiation intermittently to different portions of the at least one seed bed.

11. Apparatus according to claim 1, wherein said light radiation has a spectrum from 400 to 700 nm.

12. Apparatus according to claim 1, wherein said controllable means for applying to the seeds a number of radiation pulses of said light radiation comprises means for pulsing the light radiation at a frequency from about 10 to 150 pulses per minute, each pulse having a duration from 0.1 to 0.9 seconds, and the intervals between pulses having a duration about from 0.1 to 6.0 seconds.

13. Apparatus for promoting by light irradiation the germination of seeds and the growth of plants generated by the seeds, which comprises controllable means for impelling the seeds to travel through the apparatus, controllable means for applying to the seeds a number of radiation pulses; and means for controlling the duration of the radiation pulses and of the intervals between the radiation pulses, further comprising a rotatable drum, having inner projections for engaging and entraining the seeds as the drum rotates from a bottom to a top position and apertures for the passage of a cooling gas, wherein the inner projections comprise a plurality of longitudinal ribs and said apertures are formed in a permeable sheath stretched over said ribs, which permits the passage of the cooling gas.

14. Apparatus for promoting by light irradiation the germination of seeds and the growth of plants generated by the seeds, which comprises controllable means for impelling the seeds to travel through the apparatus, controllable means for applying to the seeds a number of radiation pulses; and means for controlling the duration of the radiation pulses and of the intervals between the radiation pulses, further comprising a rotatable drum, having inner projections for engaging and entraining the seeds as the drum rotates from a bottom to a top position and apertures for the Passage of a cooling gas, further comprising an elongated stationary envelope, coaxial with and enclosing the drum and of approximately the same length, which supports a plurality of rod-like, axially oriented, lamps, and mirror surfaces so shaped as to concentrate the light of the lamps into a narrow longitudinal strip, and comprising screen elements screening the radiation except in correspondence to said longitudinal strip.

15. Apparatus according to claim 14, wherein the seeds fall as they reach the top position from said position to the bottom, the apparatus further comprising guide surfaces for guiding the seeds to form a vertical layer, as they fall, passing in front of the narrow longitudinal strip in which the light of the lamps is concentrated.

16. Apparatus according to claim 15, further comprising angularly adjustable slats interposed between the guide surfaces, for controlling the speed of fall of the seeds and therefore the duration of their exposure to radiation.

17. Apparatus according to claim 15, further comprising reflecting means mounted opposite the narrow longitudinal strip, to reflect the concentrated light through the vertical layer formed by the seeds.

18. Apparatus for promoting by light irradiation the germination of seeds and the growth of plants generated by the seeds, comprising:

a light source for irradiating seeds with visible light simulating the solar visible spectrum in the range from about 400 nm to about 700 nm;

controllable means for impelling the seeds through the apparatus;

controllable means for selectively exposing the seeds to a plurality of radiation pulses from the light source at a frequency from about 10 to 150 pulses per minute and providing intervals between the pulses having a duration from about 0.1 to 6.0 seconds; and gas blower configured to apply to a stream of gas to cool the seeds.

* * * * *